(12) United States Patent
Anthony et al.

(10) Patent No.: US 8,226,658 B2
(45) Date of Patent: Jul. 24, 2012

(54) INSTRUMENT FOR GUIDING RESECTION OF A GREATER TUBERCLE

(75) Inventors: Sarah M. Anthony, Leesburg, IN (US); Stephen R. Donnelly, Willoughby, OH (US)

(73) Assignee: Depuy Products, Inc., Warsaw, IN (US)

( * ) Notice: Subject to any disclaimer, the term of this patent is extended or adjusted under 35 U.S.C. 154(b) by 959 days.

(21) Appl. No.: 12/118,281

(22) Filed: May 9, 2008

(65) Prior Publication Data
US 2009/0281544 A1 Nov. 12, 2009

(51) Int. Cl.
*A61F 5/00* (2006.01)
(52) U.S. Cl. .......................................... 606/87
(58) Field of Classification Search .................. 606/87, 606/96–98
See application file for complete search history.

(56) References Cited

U.S. PATENT DOCUMENTS

| | | | |
|---|---|---|---|
| 4,893,619 A | 1/1990 | Dale et al. | |
| 5,180,396 A | 1/1993 | Grollier et al. | |
| 6,045,582 A | 4/2000 | Prybyla | |
| 6,494,913 B1 | 12/2002 | Huebner et al. | |
| 6,676,662 B1 * | 1/2004 | Bagga et al. | 606/87 |
| 6,712,823 B2 | 3/2004 | Grusin et al. | |
| 6,780,190 B2 | 8/2004 | Maroney | |
| 7,198,628 B2 | 4/2007 | Ondrla et al. | |
| 7,297,162 B2 | 11/2007 | Mujwid | |
| 2002/0099381 A1 | 7/2002 | Maroney | |
| 2002/0107522 A1 | 8/2002 | Picard et al. | |
| 2003/0181984 A1 | 9/2003 | Abendschein | |
| 2004/0153066 A1 | 8/2004 | Coon et al. | |
| 2005/0055028 A1 | 3/2005 | Haines | |
| 2006/0136955 A1 | 6/2006 | Im et al. | |
| 2007/0213738 A1 | 9/2007 | Martin et al. | |

FOREIGN PATENT DOCUMENTS

| | | |
|---|---|---|
| EP | 0460886 B1 | 8/1997 |
| WO | 0071035 A | 11/2000 |
| WO | 0100096 A | 1/2001 |
| WO | WO 2006/136955 A | 12/2006 |
| WO | 2007092614 A | 8/2007 |

OTHER PUBLICATIONS

European Search Report for Corresponding Application No. 09159562.9, Dated Jan. 17, 2010, 11 Pages.
European Partial Search Report for Corresponding Application No. 09159562.9, Dated Sep. 30, 2009, 6 Pages.
European Search Report From Corresponding EPO App. No. 11190115.3-2310, Dated Jan. 20, 2012, 8 Pages.

* cited by examiner

*Primary Examiner* — Anu Ramana

(57) ABSTRACT

An instrument for use in resecting a portion of a greater tubercle of a humerus in shoulder arthroplasty is provided. The instrument includes a guide support that has a first end coupled to a long bone. The guide support extends laterally and over the greater tubercle. The instrument also includes a cutting guide movably coupled to the guide support. The cutting guide including curved frame for abutting the humerus.

19 Claims, 8 Drawing Sheets

INSTRUMENT FOR GUIDING RESECTION OF A GREATER TUBERCLE

TECHNICAL FIELD OF THE INVENTION

The present invention relates generally to the field of orthopaedics, and more particularly, to an implant for use in arthroplasty.

BACKGROUND OF THE INVENTION

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

Such joint replacement surgery is otherwise known as joint arthroplasty. Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

One type of joint replacement surgery is shoulder arthroplasty. During shoulder arthroplasty, the humeral head must be resected to allow for the insertion of a humeral stem into the intramedullary canal of the humerus. The proximal end of the humerus includes the humeral head, which articulates with the glenoid of the shoulder in a ball and socket fashion. The humeral head is nearly hemispherical in form.

The prostheses typically used for shoulder arthroplasty include a stem portion designed to extend into the intramedullary canal of the humerus and a head portion designed to replace the humeral head. The head portion of the prosthesis extends angularly from the stem portion. The resection of the natural humeral head must be made so that the angle of the cut corresponds to the angle between the stem and head portions of the prosthesis. In addition, the rotation of the cut varies to adjust to bone wear or capsular looseness.

Patients who have massive rotator cuff tears experience proximal migration of the humerus. When this occurs, part of the humeral head will contact the acromion, which can cause pain and loss of shoulder function. By providing a humeral head with an extended articulating surface, a metal surface with a low coefficient of friction will contact the acromion and reduce pain. The extended articulating surface also increases the surface of articulation in the artificial shoulder joint in abduction and external rotation.

When implanting a proximal humeral resurfacing implant with an extended articulation surface, removal of part or all of the humeral greater tubercle is needed. After the initial humeral head resection is made, a portion of the greater tubercle must also be removed. The cut that achieves this is perpendicular to the longitudinal axis of the humerus and allows for the backside of the extended articulation surface to sit on the most superior portion of the humerus.

One surgical technique used in shoulder arthroplasty is called the deltopectoral approach. This approach requires detachment of the anterior portion of the rotator cuff from the humerus in order to gain adequate exposure to the joint. This is not ideal for the patient because the disturbance of the anterior cuff can compromise the function of the shoulder.

A second technique used in shoulder arthroplasty is the anterosuperior approach. Unlike the deltopectoral approach, the anterosuperior approach spares the anterior portion of the rotator cuff. However, it requires disturbance of other soft tissue structures, namely the origin of the anterior deltoid and the acromial insertion of the coracoacromial ligament, which can also compromise shoulder function.

Clearly, neither of these approaches is ideal for the patient. What would be ideal is a third technique that spares the anterior rotator cuff, the origin of the anterior deltoid, and the insertion of the coracoacromial ligament. A soft tissue approach of this type has been identified, but there is not adequate instrumentation to guide the resection of the greater tubercle of the humerus from this approach. The soft tissue approach provides exposure to the humerus from the lateral side. Therefore, an instrument that aids the resection of the greater tubercle of the humerus from the lateral direction is needed.

SUMMARY OF THE INVENTION

According to one embodiment of the present invention, an instrument for use in resecting a portion of a greater tubercle of a humerus in shoulder arthroplasty is provided. The instrument includes a guide support having a first end coupled to the humerus. The guide support extends laterally and over the greater tubercle. The instrument also includes a cutting guide that is movably coupled to the guide support. A curved frame is included in the cutting guide and is for abutting the humerus.

According to another embodiment of the present invention, a method for resecting a greater tubercle in a humerus is provided. The method includes providing a guide support and a cutting guide. The cutting guide is moveable relative to the guide support and has a curved frame. The guide support is coupled to an instrument inserted into the humerus, such that the guide support extends laterally and over the greater tubercle. The cutting guide is coupled to the guide support and the cutting guide is adjusted so that the curved frame abuts a portion of the humerus. The cutting guide is secured in a position relative to the guide support and the greater tubercle is resected.

According to yet another embodiment of the present invention, an instrument for guiding the resection of a greater tubercle of a humerus is provided. The humerus has a longitudinal axis. The instrument includes a guide support in a fixed position relative to the humerus. The guide support extends laterally and over the greater tubercle. A cutting guide is moveably coupled to the guide support. The cutting guide is adapted to guide the resection of the greater tubercle at an angle perpendicular to the longitudinal axis.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1A:
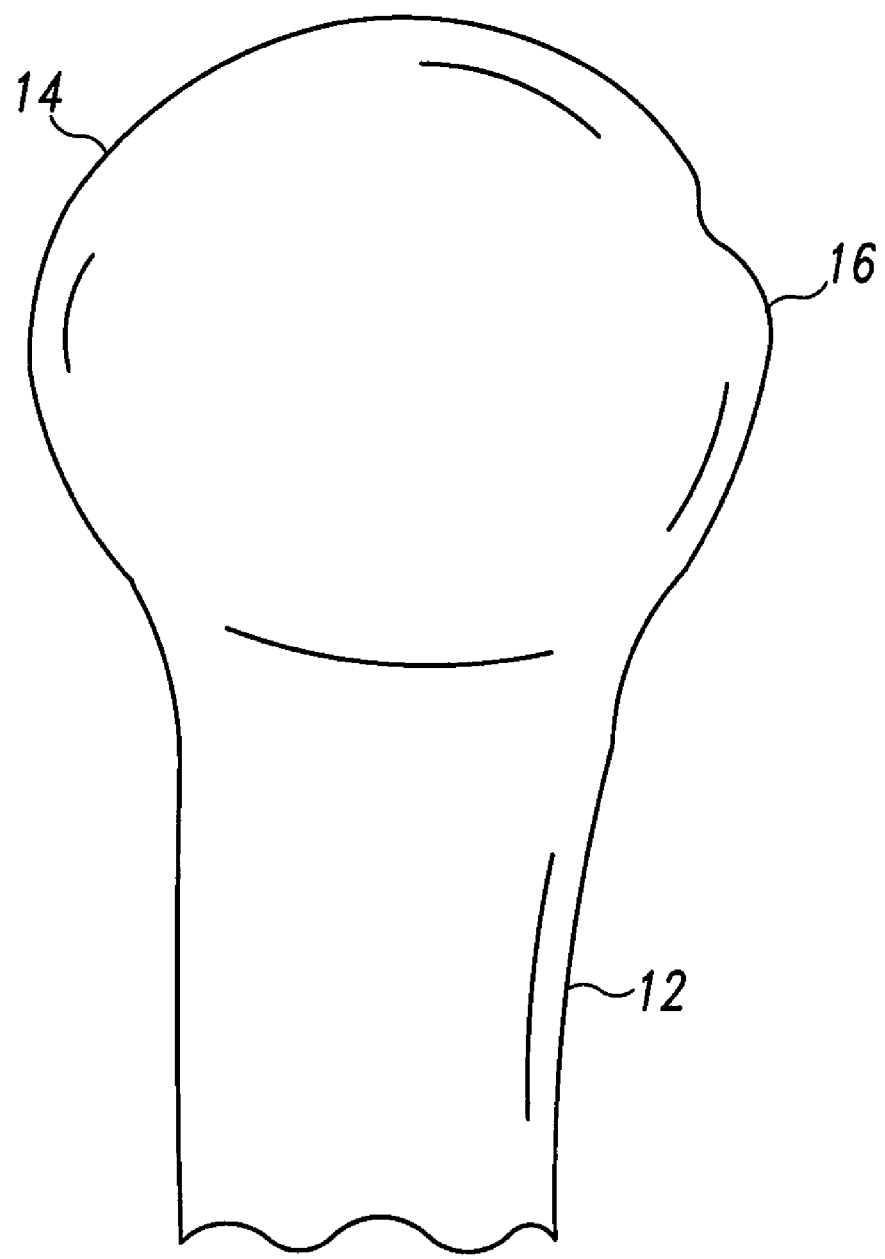
FIG. 1A is a perspective view of a humerus.
Figure 1B:
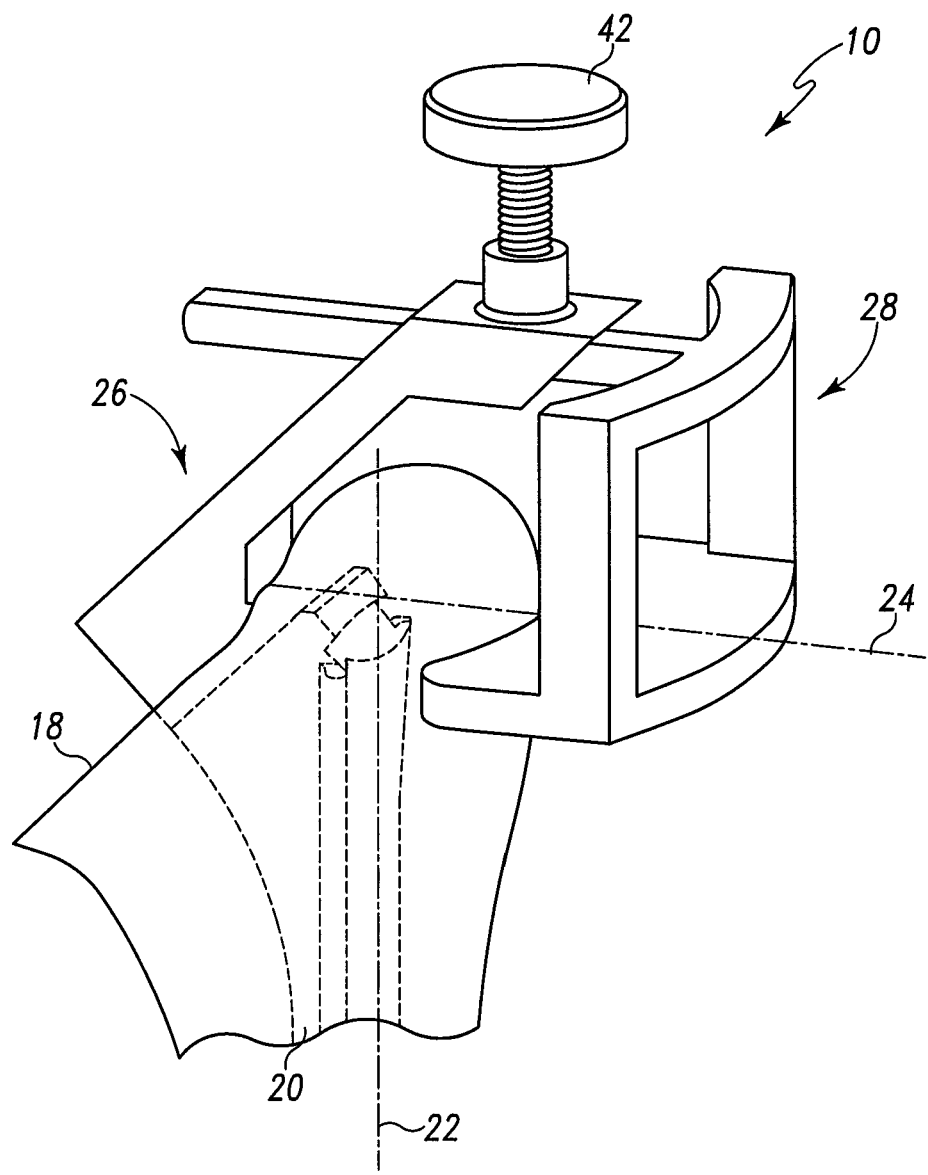
FIG. 1B is a perspective view of an instrument according to one embodiment of the present invention on a humerus, with the humeral head resected.
Figure 1C:
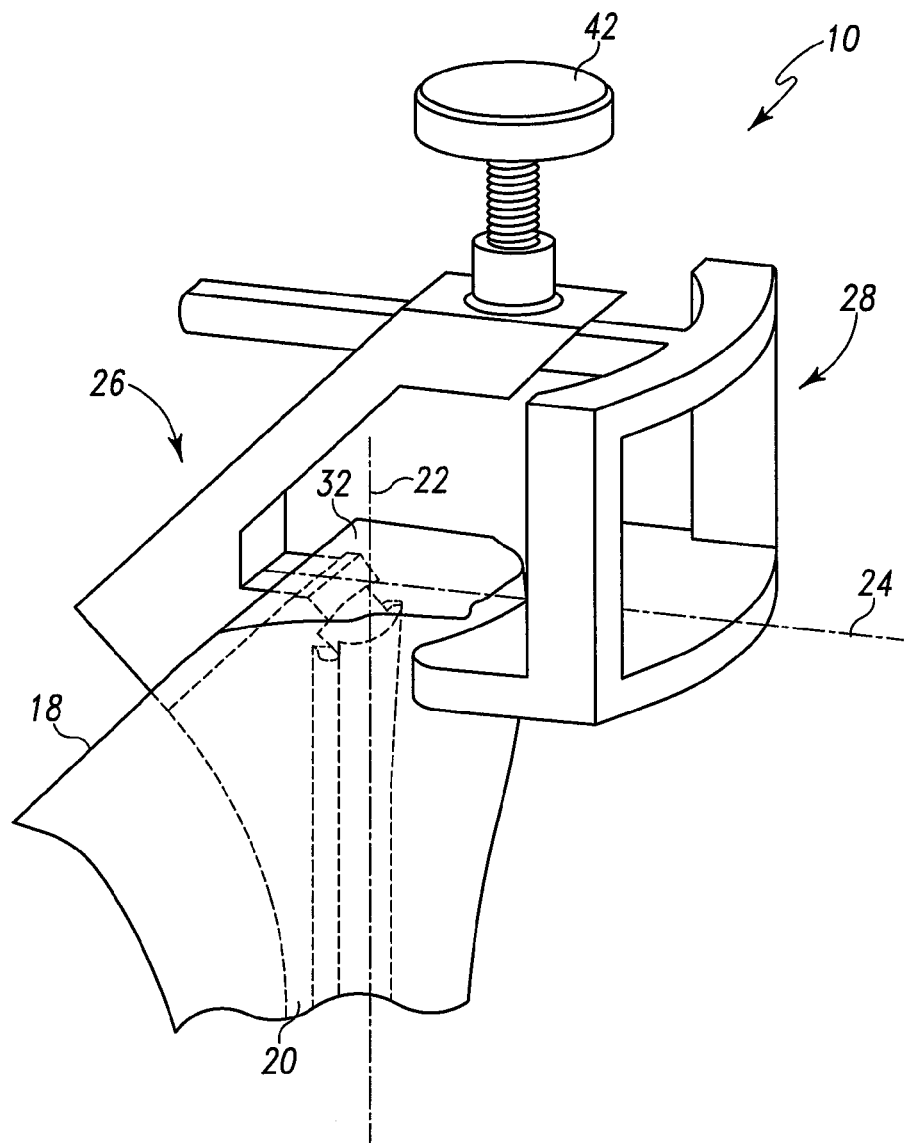
FIG. 1C is a perspective view of the instrument of FIG. 1B on the humerus with also the greater tubercle resected.

FIGS. 1A-1C illustrate a shoulder arthroplasty and an instrument 10 according to one embodiment of the present invention. Turning first to FIG. 1A, a humerus 12 is shown. The humerus 12 includes a humeral head 14 and a greater tubercle 16. During shoulder arthroplasty, the humeral head 14 is resected, resulting in a planar surface 18, as shown in FIG. 1B. After the humeral head 14 is resected, a broach 20 is inserted into the humerus 12. As shown, the planar surface 18 is at an angle to both a longitudinal axis 22 and a medial-lateral axis 24. During the shoulder arthroplasty, the humeral head 14 would be resected and a cavity will be prepared in the humerus 12 to receive a stem of an implant.

As shown in FIG. 1B, the instrument 10 includes a guide support 26 and a cutting guide 28. The guide support 26 is at an angle that is parallel to the surface of the broach 20. Preferably, the guide support 26 is also parallel to the planar surface 18 of the resected humeral head 14. In some embodiments, the angle between the guide support 26 and the longitudinal axis 22 is between about 30 degrees and about 60 degrees. In some embodiments, the angle is between about 40 degrees and about 50 degrees. The guide support 26 couples to a cutting guide arm 30 of the cutting guide 28. The cutting guide 28 includes a cutting surface that abuts the lateral edge of a greater tubercle 16. The cutting guide 28, as will be described later, is used to resect the greater tubercle 16 to create a flat planar surface 32 (FIG. 1C) that is parallel to the medial-lateral axis 24 and perpendicular to the longitudinal axis 22.

Figure 2:
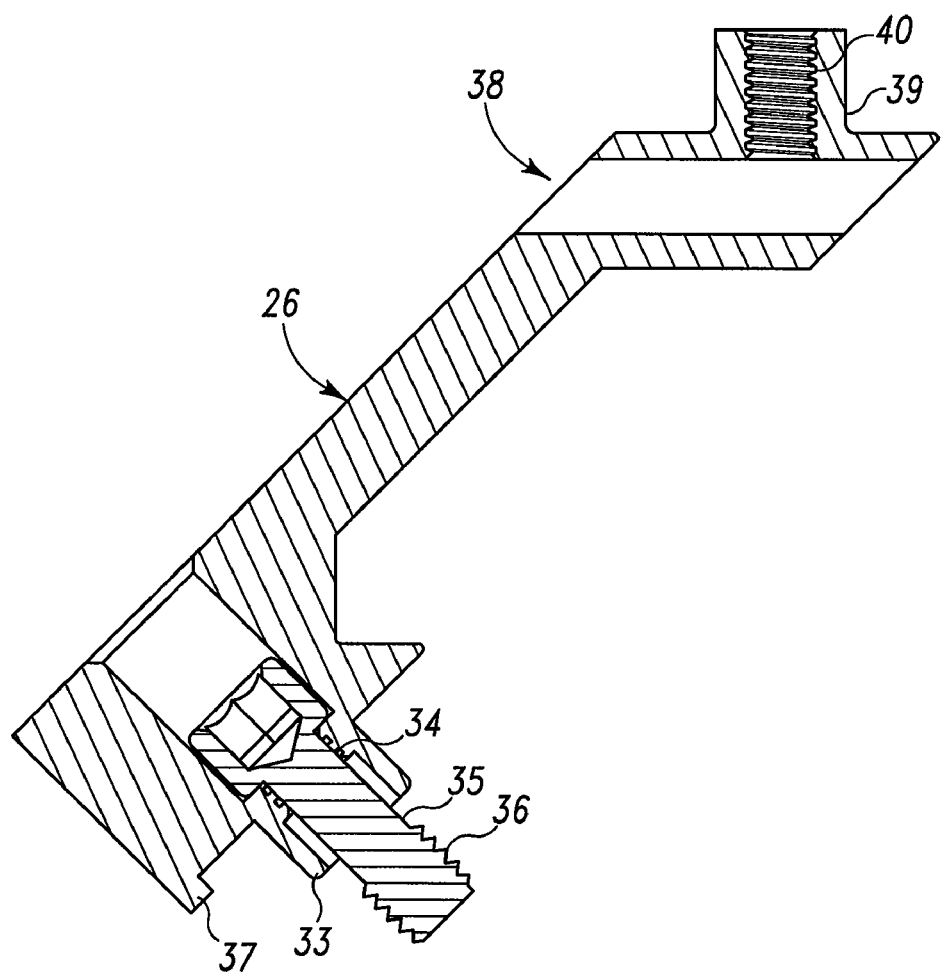
FIG. 2 is a sectional side view of a guide support of the instrument of FIG. 1.

Turning now to FIG. 2, a sectional side view of the guide support 26 will be described. One end of the guide support 26 includes a stud 33 for placement in the broach 20. In the illustrated embodiment, the stud 33 includes threads 34 for engaging a captured screw 35. The captured screw 35 includes threads 36 for engaging the broach 20 (FIG. 1) placed in the cavity of the humerus 12. It should also be understood that other locking mechanisms such as taper locks, locking tabs, bolts, quick connects, ball plungers, etc. . . . may be used. The stud 33 is used to lock the guide support 26 in position relative to the broach 20. It is important to note that the guide support 26 extends off of the broach 20 and out of the shoulder joint in the lateral direction, which allows for a lateral approach for resection of the greater tubercle 16. An anti-rotation flange 37 is included that mates with the broach 20 to prevent the guide support 26 from rotating relative to the broach 20.

At the other end of the guide support 26 is a guide support slot 38 for receiving the cutting guide 28 as will be described below. Above the slot 38 is a boss 39. The boss 39 includes a locking member 40, in the illustrated embodiment, threads, for engaging a knob 42 (FIG. 1) that will secure the guide support 26 to the cutting guide 28. Although threads 40 and the knob 42 are shown, other known locking mechanisms, such as taper locks, locking tabs, bolts, quick connects, ball plungers, ratchets, teeth, etc. . . . may be used.

Figure 3:
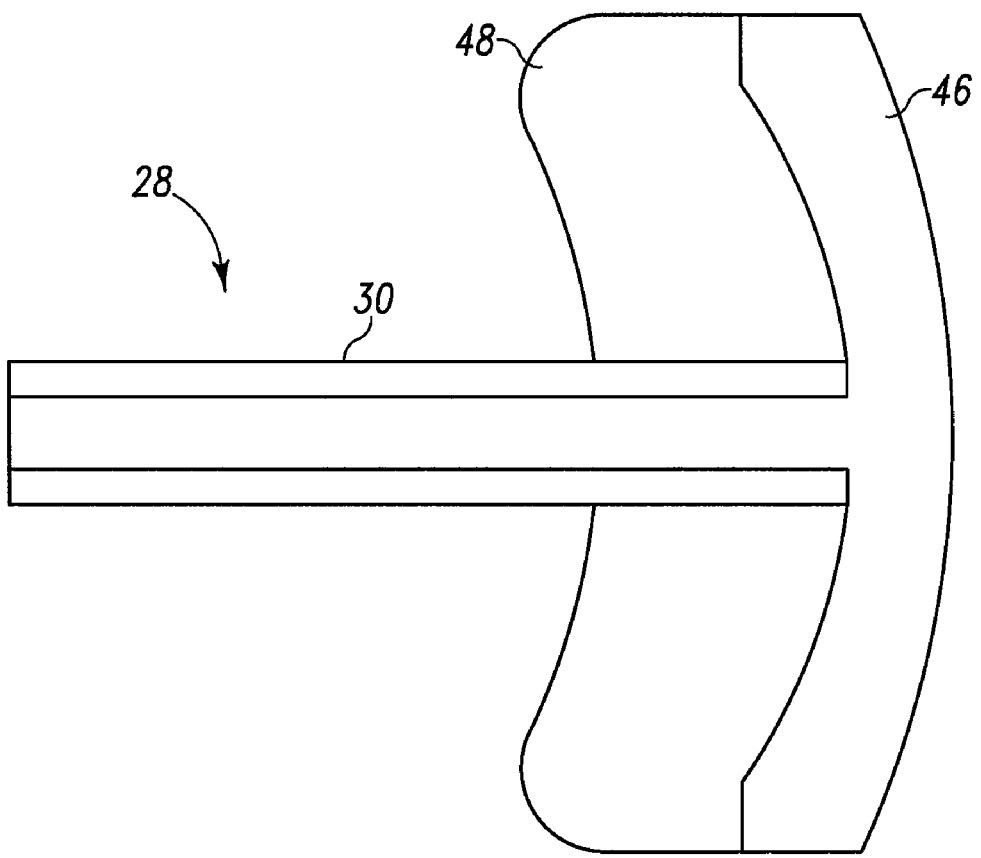
FIG. 3 is a top view of a cutting guide of the instrument of FIG. 1.

Turning now to FIG. 3, the cutting guide 28 according to one embodiment of the present invention will be described. As shown in FIG. 3, the cutting guide 28 includes the cutting guide arm 30 that couples to the guide support 26 by sliding into the cutting guide slot 38 and locking the arm 30 into position via the boss 39. Because the cutting guide slot 38 has a width that is larger than the width of the cutting guide arm 30, the cutting guide arm 30 can be adjusted slightly about the longitudinal axis 22. The cutting guide arm 30 can also be easily slid through the cutting guide slot 38 prior to tightening the knob 42 to obtain the optimal location for the cutting guide 28 relative to the humerus 12.

The cutting guide 28 also includes a curved frame 46. The curved frame 46 includes a cutting surface 48 that is curved so as to nest against the outer portion of the humerus 12. The curve of the cutting surface 48 is designed to closely resemble the radius of curvature of the humerus 12. In some embodiments, the curve of the cutting surface 48 has a radius of between about 20 cm and 30 cm. In some embodiments, the curve of the cutting surface 48 has a radius of between about 22 cm and 26 cm.

As shown in FIG. 1B, the cutting guide arm 30 is slidably engagable with the guide support 26. The knob 42 is turned to lock the cutting guide arm 30 in the desired position relative to the humerus 12. During use, the surgeon would slide the cutting saw along the top part of the cutting surface 48 to resect the greater tubercle 16, leaving the planar surface 32 as shown in FIG. 1C. Although the illustrated embodiment shows a smooth arm, the cutting guide arm 30 could include teeth. In such an embodiment, the knob 42 would be a push-button that includes a ratchet or gear for engaging the teeth. When pressed, the push button would release the teeth.

Figure 4:
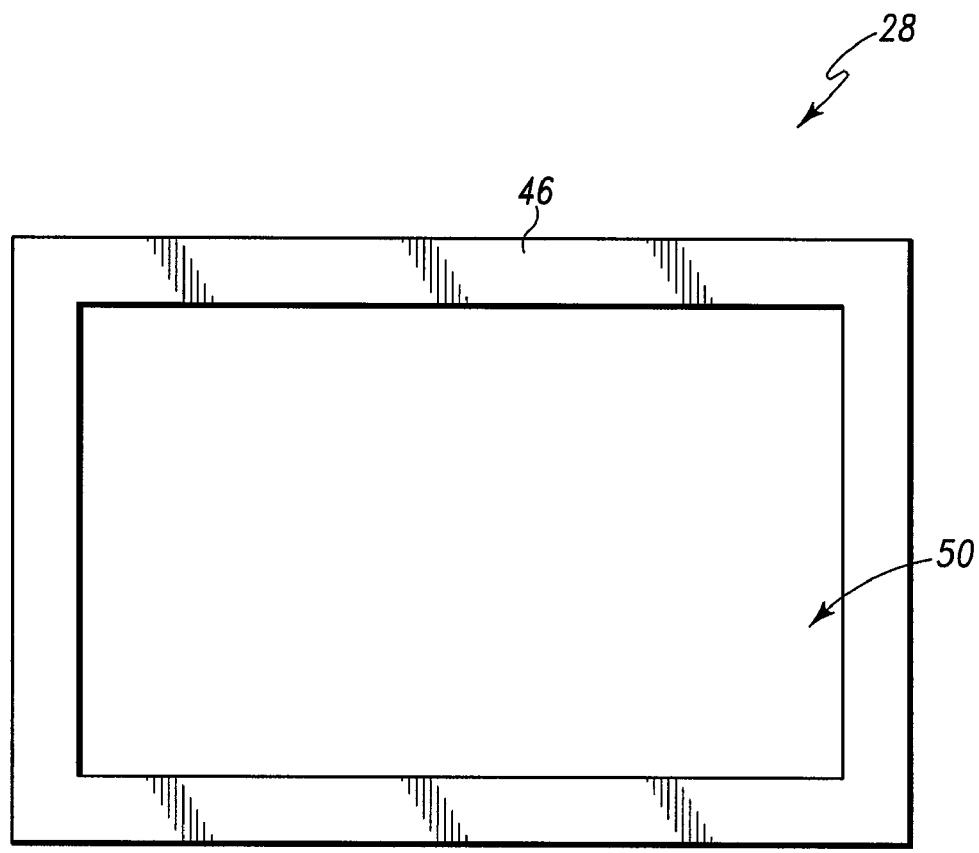
FIG. 4 is a front view of the cutting guide of FIG. 3.
Figure 5:
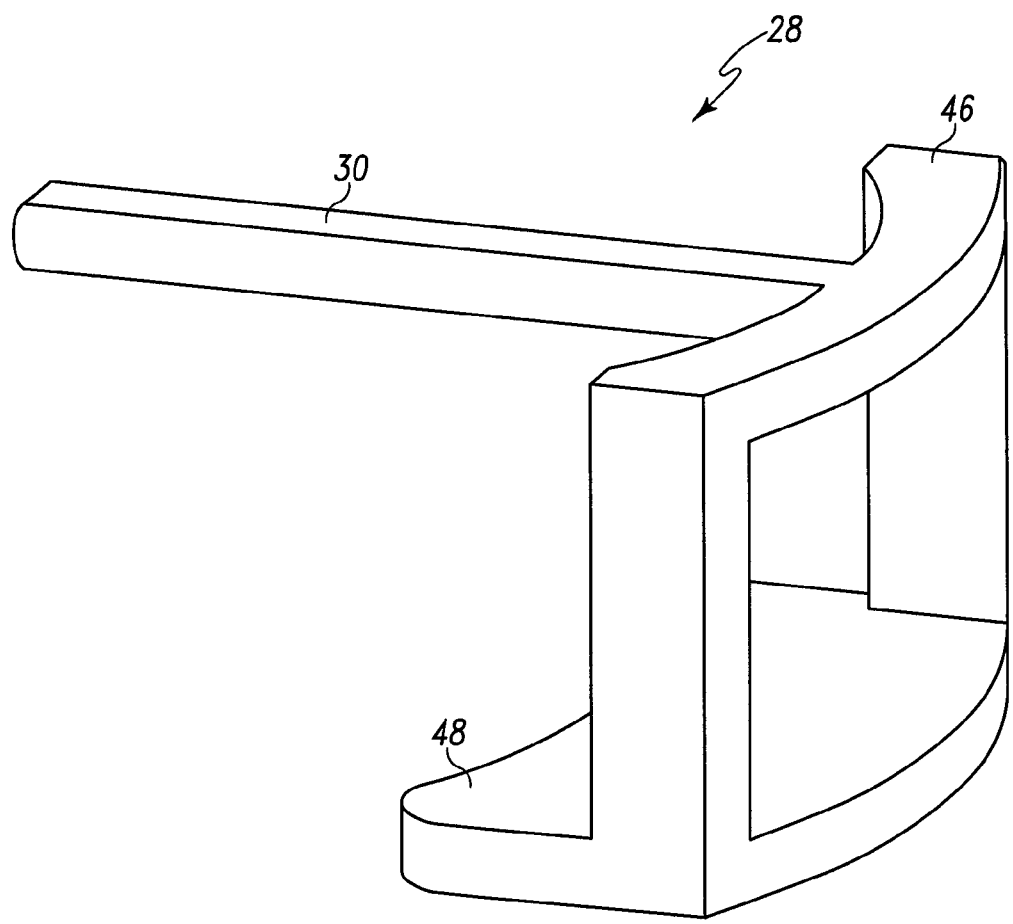
FIG. 5 is an isometric view of the cutting guide of FIG. 3.

Turning now to FIG. 4, a front view of the cutting guide 28 is shown. As shown, the curved frame 46 creates a viewing area 50. The viewing area 50 allows the surgeon to view the cutting area during the surgery. As shown in FIGS. 3 and 5, the viewing area 50 is curved, creating a large open area for the surgeon to view the cutting area. As discussed above, when the surgeon is inserting the cutting guide arm 30 into the guide support slot 38, the surgeon can toggle the cutting guide arm 30 relative to the guide support 26, which moves the frame 46. By being able to move the frame 46, the surgeon can adjust the viewing area 50 to best view the surgical area.

Figure 6:
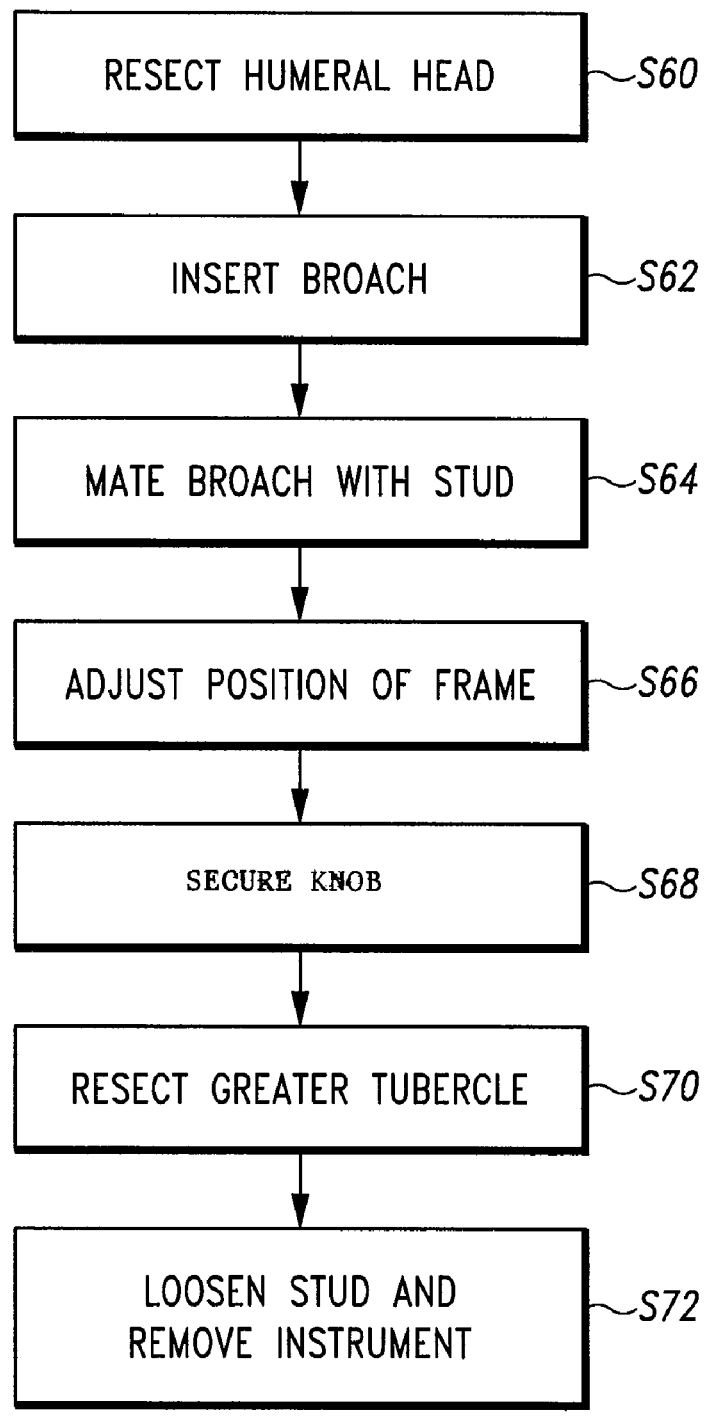
FIG. 6 is a flow chart describing a method of using an instrument according to one embodiment of the present invention.

Turning now to FIG. 6, a flow chart of the use of an instrument according to one embodiment will be described. First, at step s60, the humeral head 14 is resected and the broach 20 is inserted at step s62. At step s64, the broach 20 is mated with the stud 33 to affix the guide support 26 to the humerus 12. The cutting guide arm 30 is then placed in the guide support slot 38 and translated until the curved cutting surface 48 of the cutting guide 28 contacts the humerus 12. If desired, the surgeon at step s66 can adjust the cutting guide 28 to obtain the optimal line of sight and placement of the cutting tool. Then, at step s68, the knob 42 is used to secure the cutting guide 28 in place. The cutting tool (not shown) is then placed on top of the cutting surface 48 and used to resect the greater tubercle 16 at step s70. After the resection is complete, the stud 33 is loosened and the entire instrument 10 can be removed from the broach 20 (step s72). Trialing and implantation can follow as known in the art. In some embodiments, the instrument 10 is made of stainless steel. The stainless steel may also be coated, so as to protect against wear. In other embodiments, other medical grade metals or materials may be used.

Although the present invention and its advantages have been described in detail, it should be understood that various changes, substitutions, and alterations can be made therein without departing from the spirit and scope of the present invention as defined by the appended claims.

The invention claimed is:

1. An instrument for use in resecting a portion of a greater tubercle of a humerus in shoulder arthroplasty, the instrument comprising:

a guide support having a first end adapted to be coupled to the humerus, the guide support configured to extend laterally and over the greater tubercle; and a cutting guide movably coupled to the guide support, the cutting guide including a curved frame configured to abut a lateral edge of the greater tubercle, wherein the cutting guide includes a guide arm and the guide support includes a slot for receiving the guide arm, such that the guide arm can slide through the slot.

2. The instrument of claim 1, wherein the curved frame defines a viewing window for viewing an area of the long bone to be resected.

3. The instrument of claim 1, wherein the long bone defines a longitudinal axis and the guide support extends at an angle of approximately 45 degrees from the longitudinal axis of the long bone.

4. The instrument of claim 3, wherein the cutting guide includes a cutting guide arm that is coupled to the guide support perpendicularly to the longitudinal axis.

5. The instrument of claim 3, wherein the cutting frame includes a cutting surface and the cutting surface is perpendicular to the longitudinal axis.

6. The instrument of claim 1, further comprising a stud for coupling the guide support to a second instrument inserted in the long bone.

7. The instrument of claim 1, further comprising a knob for locking the cutting guide in a position relative to the guide support.

8. A method for resecting a greater tubercle in a humerus comprising:

providing a guide support and a cutting guide, the cutting guide being moveable relative the guide support, the cutting guide having a curved frame;

coupling the guide support to an instrument inserted into the humerus, such that the guide support extends laterally and over the greater tubercle;

removably coupling the cutting guide to the guide support;

adjusting the cutting guide so that the curved frame abuts a portion of the humerus;

securing the cutting guide in a position relative to the guide support; and resecting the greater tubercle.

9. The method of claim 8, wherein coupling the guide support to an instrument inserted into the humerus includes threading a screw in the guide support into the instrument in the humerus.

10. The method of claim 8, further comprising adjusting the curved frame about a longitudinal axis of the humerus prior to securing the cutting guide in a position relative to the guide support.

11. An instrument for guiding the resection of a greater tubercle of a humerus, the humerus having a longitudinal axis, the instrument comprising:

a guide support in a fixed position relative to the humerus, the guide support configured to extend laterally and over the greater tubercle; and a cutting guide moveably coupled to the guide support, the cutting guide including a curved frame configured to abut a lateral edge of the greater tubercle the cutting guide adapted to guide the resection of the greater tubercle at an angle perpendicular to the longitudinal axis, wherein the cutting guide includes a guide arm and the guide support includes a slot for receiving the guide arm, such that the guide arm can slide through the slot.

12. The instrument of claim 11, wherein the guide support includes a stud for locking to a second instrument that is inserted in the humerus.

13. The instrument of claim 11, wherein the guide support includes a knob that extends through the slot for locking the guide arm in a position relative to the guide support.

14. The instrument of claim 11, wherein the slot has a width greater than the width of the guide arm, so that the guide arm can be rotated about the longitudinal axis.

15. The instrument of claim 11, wherein the cutting guide includes a frame, the frame defining a viewing window.

16. The instrument of claim 15, wherein the frame includes a curved cutting surface, the curved cutting surface having a radius between about 20 cm to about 30 cm.

17. The instrument of claim 11, wherein the instrument is made of stainless steel.

18. The instrument of claim 11, wherein the guide support extends at an angle between about 30 degrees and about 60 degrees from the longitudinal axis.

19. The instrument of claim 11, wherein the guide support is secured to an instrument in the humerus and the guide support includes an anti-rotation flange that couples to the instrument.

\* \* \* \* \*